US006126683A

United States Patent [19]
Momtaheni

[11] Patent Number: 6,126,683
[45] Date of Patent: Oct. 3, 2000

[54] DEVICE FOR THERAPEUTIC TREATMENT OF THE TEMPOROMANDIBULAR AND MAXILLOMANDIBULAR REGION AND METHOD FOR USING SAME

[76] Inventor: David M. Momtaheni, 13 Campden Rd., Scarsdale, N.Y. 10583

[21] Appl. No.: 09/224,780

[22] Filed: Jan. 4, 1999

[51] Int. Cl.⁷ .................................. A61F 7/00; A61F 5/00
[52] U.S. Cl. ........................ 607/109; 607/110; 607/108; 602/17; 602/13
[58] Field of Search .................................. 607/108, 109, 607/110; 602/13, 17

[56] References Cited

U.S. PATENT DOCUMENTS

| | | | |
|---|---|---|---|
| Re. 34,661 | 7/1994 | Grim | 602/27 |
| Re. 34,883 | 3/1995 | Grim | 602/13 |
| 3,171,410 | 3/1965 | Towle, Jr. et al. | |
| 3,687,143 | 8/1972 | Schneeberger et al. | |
| 3,871,381 | 3/1975 | Roslonski | |
| 4,190,054 | 2/1980 | Brennan | 128/402 |
| 4,527,566 | 7/1985 | Abare | 128/402 |
| 4,702,235 | 10/1987 | Hong | 128/78 |
| 4,934,357 | 6/1990 | Frantzich et al. | 127/164 |
| 5,020,536 | 6/1991 | Keen | 128/402 |
| 5,031,609 | 7/1991 | Fye | 128/163 |
| 5,109,841 | 5/1992 | Hubbard et al. | 128/380 |
| 5,148,804 | 9/1992 | Hill et al. | 128/402 |
| 5,169,384 | 12/1992 | Bosniak et al. | 604/20 |
| 5,188,103 | 2/1993 | Smith | 128/380 |
| 5,378,042 | 1/1995 | Daneshvar | 297/393 |
| 5,407,421 | 4/1995 | Goldsmith | 602/5 |
| 5,411,541 | 5/1995 | Bell et al. | 607/104 |
| 5,431,622 | 7/1995 | Pyrozyk et al. | 602/2 |
| 5,449,379 | 9/1995 | Hadtke | 607/104 |
| 5,658,324 | 8/1997 | Bailey, Sr. et al. | 607/104 |
| 5,687,743 | 11/1997 | Goodwin | 128/848 |

*Primary Examiner*—Linda C. M. Dvorak
*Assistant Examiner*—Jaclyn Debra Ram
*Attorney, Agent, or Firm*—St. Onge Steward Johnston & Reens LLC

[57] ABSTRACT

A device to treat the temporomandibular and maxillomandibular region of patient with cryo, thermal and/or compression therapy is disclosed. The device comprises a fabric layer anatomically designed to contact the temporomandibular joint and the maxillomandibular region, an inflatable layer, and a heater for heating the masticatory muscles, the temporomandibular joint and temporal regions. In an alternative embodiment, a device comprises a fabric layer designed to contact the maxillomandibular region, an inflatable layer, a hard plate placed on said fabric layer to resist bulging of said inflatable layer when inflated, and a conductive layer covering said inflatable layer. Methods to use the device to treat the maxillomandibular region and temporomandibular joint of a patient are also disclosed.

9 Claims, 3 Drawing Sheets

DEVICE FOR THERAPEUTIC TREATMENT OF THE TEMPOROMANDIBULAR AND MAXILLOMANDIBULAR REGION AND METHOD FOR USING SAME

FIELD OF THE INVENTION

The present invention relates to a medical treatment device for the application of cryo, thermal, and compression therapy to an injured or traumatized region of the face and jaw. More specifically, the present invention is directed to a garment device to treat the tempomandibular joint and its disorders with cryo, thermal, and/or compression therapy, and to treat the maxillo-mandibular regions with cryo compression therapy, with an integral and portable unit worn by the patient.

BACKGROUND OF THE INVENTION

A variety of medical conditions which can cause inflammation of the joint or masticatory muscles can have immediate relief by reduction of the temperature to the region. The effect of cooling and compression on traumatically injured soft and hard tissues has been well known and documented in the medical, dental and surgical literature. Cold application with compression reduces edema (swelling) and the flow of blood to the inflamed tissue of injured muscles, tendons, and ligaments and has been used for over a century. Thus the art teaches various configurations for ice pack compresses or introduction of a cooling medium with compression. On the other hand, a variety of medical conditions can create reduction of tissue blood flow, ischemia, and muscle ache, myalgia, to a region such as the masitcatory (chewing) muscles. The literature supports that pain resulting from such a condition is relieved by thermal application with heating to the injured muscles. Application of heat to such areas increases the blood flow to the region and promotes healing.

Temporomandibular disorders (TMD) refer to a collection of medical and dental conditions affecting the temporomandibular joint (TMJ), that being the joint near the temple and the lower part of the jaw, and/or the muscles of mastication (chewing), as well as contiguous components. Although specific etiologies such as degenerative arthritis and trauma underlie some TMD, as a group these conditions have no common etiology or biological explanation and comprise a hetereogeneous group of health problems whose signs and symptoms are overlapping, but not necessarily identical. Consequently, depending on the condition, application of heat, cold, or compression or a combination thereof, may or may not be beneficial. For example, in the case of direct trauma to the TMJ and for reduction of post-operative swelling and hemorrhage, cryo compression treatment to specific areas associated with the TMJ can have a favorable effect. However, for TMJ degenerative joint disease (DJD) and arthritic conditions, thermal therapy only should be delivered to the TMJ region. In the case of post-traumatic hemorrhage to the maxillofacial (cheek) region, post-operative elective maxillo-mandibular osteomies and removal of wisdom teeth, cryo compression therapy is effective.

Although various garments and bandages for use on the facial region have been proposed, the prior art has not specifically addressed the use of an appropriate device for treating the above TMJ disorders, or more generally, the areas of the TMJ and lower jaw.

For example, U.S. Pat. No. 4,190,054 (Brennan) discloses a bandage in the form of a complete face mask necessary to hold facial tissues after cosmetic surgery to prevent sagging. The bandage incorporates a plurality of attachment points located on its outside for conventional hot or cold packs.

U.S. Pat. No. 5,188,103 (Smith) teaches the use of an adjustable facial dressing for compression and/or support with means to apply thermal or cryo treatment via a pouch for conventional hot or cold packs.

U.S. Pat. No. 3,871,381 (Rolonski) teaches the use of a pressurized volatile refrigerant cooling a serpentine channel in a flexible device through a controlled flow valve. Rolonski discloses a device embodied in an application for a race horse, a human hand, foot, and knee with the provision for only compression and cooling.

U.S. Pat. No. 5,658,324 (Bailey, Sr. et al.) similarly discloses an apparatus for providing cryo therapy and controlled compression using a maze with a plurality of blind pockets forming traps. The maze terminates in a port inflating a bladder with the vaporized refrigerant to a specified pressure.

U.S. Pat. No. Re. 34,883 (Grim) discloses an orthopaedic back support comprising an elastic material which carries a gel pad with an adjustable heating element and an air bladder. The gel material is specifically suited to orthopaedic applications to comfort the patient. The heating element contained therein forms a separate pouch that is closest to the patient's back and which covers the air pumped inflatable layer underneath.

U.S. Pat. No. 5,449,379 (Hadtke) is directed to an apparatus for applying heat or cold and pressure to an injured area with three layers of flexible material. An inflation chamber is formed for a pressurized gas to provide compression. The particular compressed gas employed determines the temperature of the wrap. Heating can be provided in communication with same inflation chamber via a two phase mixture of gases to produce an exothermic reaction.

A disadvantage to the prior art is that none of the devices is suitable for treating TMD because none of the devices have a specific anatomical design which can render controlled hot and cold compression to the masticatory muscles. In addition, none of the devices are designed to provide a sustainable heat source to the TMJ region readily controllable by the patient. Moreover, the design of other types of cryo/thermal compression devices appropriate for other medical applications do not have the ability to provide a sustainable cold source, controllable by the patient, without either having to provide a different gas supply or to replace the thermal system with the cryo system. Furthermore, application of heat by the use of two-phase gases to produce an exothermic reaction as disclosed by Hadtke produces compression which is not beneficial in the healing phase as it can reduce the blood supply to the injured tissue which can be counterproductive. As such, none of the prior devices are appropriate to the pathophysiology of the disease process within the joint and muscles associated with the TMJ and maxillomandibular region.

Another disadvantage to other cryo/thermal compression systems is any inflation to provide compression ultimately causes the flexible device to bulge, which can render a device applied to the TMJ and maxillomandibular region less effective and cumbersome to the patient.

Yet another disadvantage to the prior art systems which employ any combination of compression with cryo and/or thermal therapy is the complexity of design associated with multi-channeled inflation chambers to control the contact of the device with a cryo gas and temperature adjacent to the patient.

What is desired, therefore, is device suitable in anatomical design to apply both cryo, thermal and compression therapy effective for specific treatment of TMJ disorders, and the maxillomandibular region of a patient. What is also desired is a device, wherein the temperature and pressure can be readily controlled and sustained by the patient without having to forego either cryo therapy, or thermal therapy with the same device, and wherein the patient can change from either cryo therapy with compression, or thermal therapy, without having to alter the device. What is also sought is device for treating TMJ disorders with improved compression, wherein bulging of the inflated device is reduced.

SUMMARY OF THE INVENTION

Accordingly, it is the object of the present invention to provide a device to treat the temporomandibular joint (TMJ) and maxillomandibular region of a patient with the option of cryo, thermal, or compression therapy in a single integral unit.

It is another object of the present invention to provide a device to treat the TMJ and maxillomandibular region of a patient anatomically designed to provide cryo and compression therapy and/or thermal therapy specifically to the angle of the lower jaw where most traumatic injuries, such as mandibular fractures, occur and/or to the angle of the jaw and the TMJ.

It is a further object of the present invention to provide a device to treat the TMJ and maxillomandibular region of a patient with a sustainable heat source readily controlled by the patient.

It is another object of the present invention to provide a device to treat the TMJ and maxillomandibular region of a patient with a sustainable cold source, controlled by the patient, without either having to provide a different gas supply or to replace a thermal system with a cryo system.

It is a further object of the present invention to provide a device to treat the TMJ and maxillomandibular region of a patient with an inflation bladder that is simpler in construction and more economical to manufacture than other devices that employ cryo compression therapy.

Another object of the present invention is to provide a device to treat the TMJ and maxillomandibular region of a patient that is constructed to direct compression to the appropriate anatomical area for treating TMJ disorders and the maxillomandibular region that resists bulging rendering the device more effective or less cumbersome to the patient.

Yet a further object of the present invention is to provide a method to use a device to treat a patient with the option of cryo, thermal or compression therapy appropriate to the pathophysiology of disease processes within the joint and muscles associated with the TMJ and maxillomandibular regions.

To overcome the deficiencies of the prior art and to achieve some of the objects and advantages listed above, the present invention provides: a device to treat the temporomandibular joint of a patient constructed for cryo, thermal, and compression therapy, a device to treat maxillomandibular region of a patient constructed for cryo and compression therapy, a method to use a device to treat the maxillomandibular region of a patient with cryo, and compression therapy, and a method to use a device to treat the temporomandibular joint of a patient with cryo thermal and compression therapy.

The device to treat the temporomandibular joint of a patient according to the invention comprises: a fabric layer anatomically designed to contact the temporomandibular joint, the chin and the parietal area of a patient, having an extension around the angle of the jaw and the temporomandibular joint; an inflatable layer to direct compression to the temporomandibular joint, the inflatable layer attached to the fabric layer, and a heater for heating the masticatory muscles, the temporomandibular joint and temporal regions, the heater attached to the fabric layer.

The device to treat the maxillomandibular region of a patient according to the invention comprises: a fabric layer anatomically designed to contact the maxillomandibular region, the chin and the parietal area of a patient, having an extension around the angle of the jaw; an inflatable layer to direct compression to the maxillomandibular region; the inflatable layer attached to the fabric layer; and a hard plate placed on the fabric layer, wherein the plate is lateral to the patient's skin to resist bulging of the inflatable layer when inflated.

In another embodiment, the invention provides a device to treat the maxillomandibular region or the temporomandibular joint of a patient further comprising a conductive layer covering the inflatable layer.

The invention in one of its aspects also provides a method to use a device to treat the maxillomandibular region of a patient with cryo, and compression therapy. Such a method comprises the steps of: wrapping a device to contact the maxillomandibular region, the chin and the parietal area of a patient by use of an extension around the angle of the jaw; inflating the device to apply a pressure to the maxillomandibular region; and cooling a conductive layer of the device, wherein the conductive layer contacts the maxillomandibular region.

In another aspect, the invention provides a method to use a device to treat the temporomandibular joint of a patient with cryo and compression therapy comprising the steps of: wrapping a device to contact the temporomandibular joint, the chin and the parietal area of a patient by use of an extension around the angle of the jaw; inflating the device to apply a pressure to the temporomandibular joint region; cooling a conductive layer of the device, wherein the conductive layer contacts the temporomandibular joint region; and heating the device to supply direct heat to the masticatory muscles, the temporomandibular joint and temporal regions.

The invention and its particular features and advantages will become more apparent from the following detailed description when considered with reference to the accompanying drawings.

DETAILED DESCRIPTION OF THE INVENTION

Figure 1:
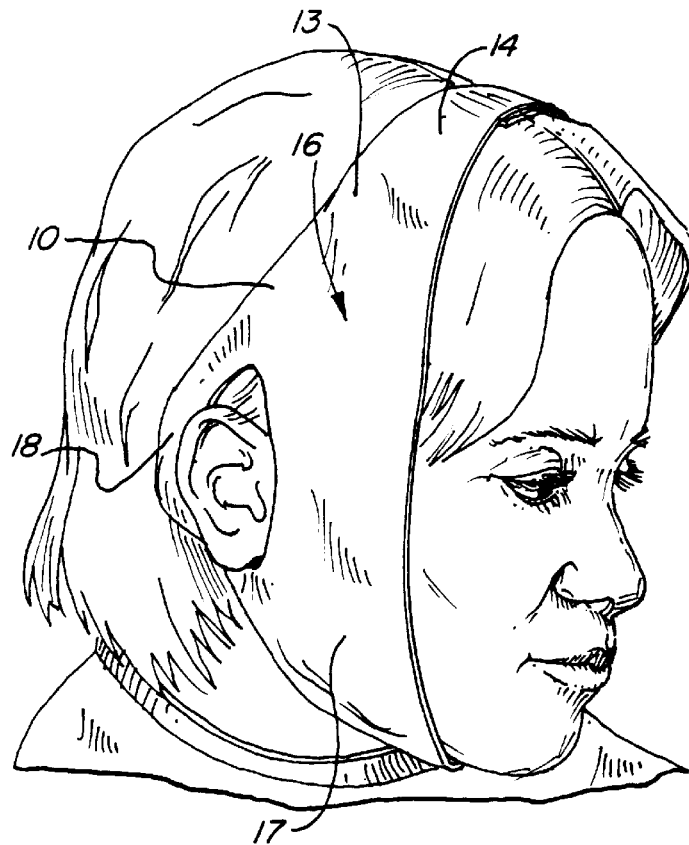
FIG. 1 is a pictorial view of the garment device of the present invention used to treat tempomandiblar joint disorders and the maxillomandibular region as worn by the patient.

Referring to the drawings in detail, FIG. 1 depicts the garment device of the present invention with a fabric layer 10 anatomically designed to treat tempomandiblar joint disorders and the maxillomandibular region of a patient. As such, fabric layer 10 comprises two auricular regions 12 for accommodating the patient's ears, a temporal region 13, two parietal bands or straps 14 for joining each end of fabric layer 10 together in the parietal area of the patient, and a temporomandibular joint (TMJ) region 16. The fabric layer 10 is secured to the patient's head via parietal straps 14 which in turn are joined by VELCRO® strips 15 attached to straps 14. The fabric layer 10 is further secured to the patient by a masseteric region 17 that extends around and under the patient's jaw. In addition, post auricular bands 18 are placed around the patient's ears which also aide in securing the fabric layer 10. The bands 18 function to provide a snug fit which reduces the likelihood that fabric layer 10 will slip from optimum contact with the patient's tempomandiblar joint and the maxillomandibular region.

Figure 2:
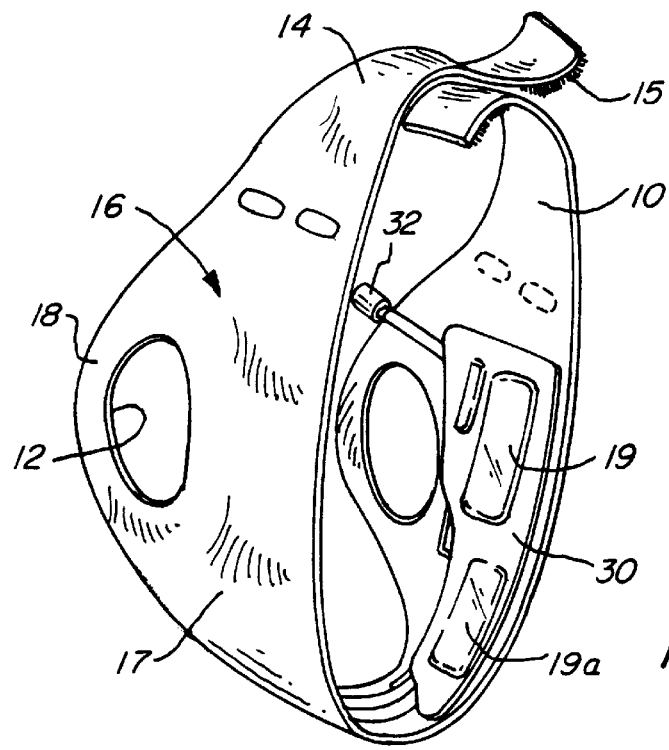
FIG. 2 is a pictorial view of the garment device of FIG. 1 showing the relative position of the layers and interior components of the present invention.
Figure 3:
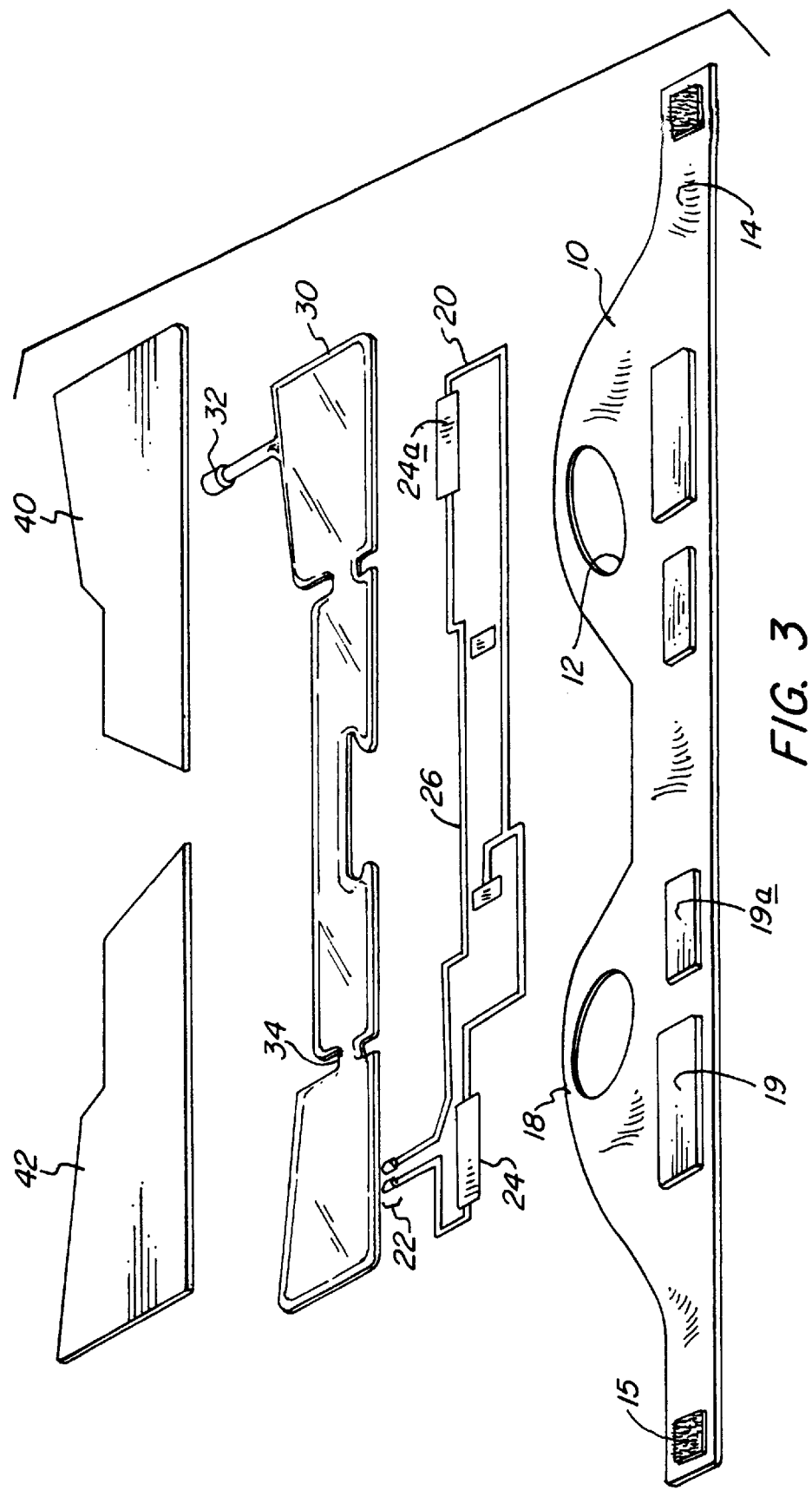
FIG. 3 is an exploded view of the garment device of FIG. 1 showing the relative placement of all of the components and layers of the present invention.
Figure 4:
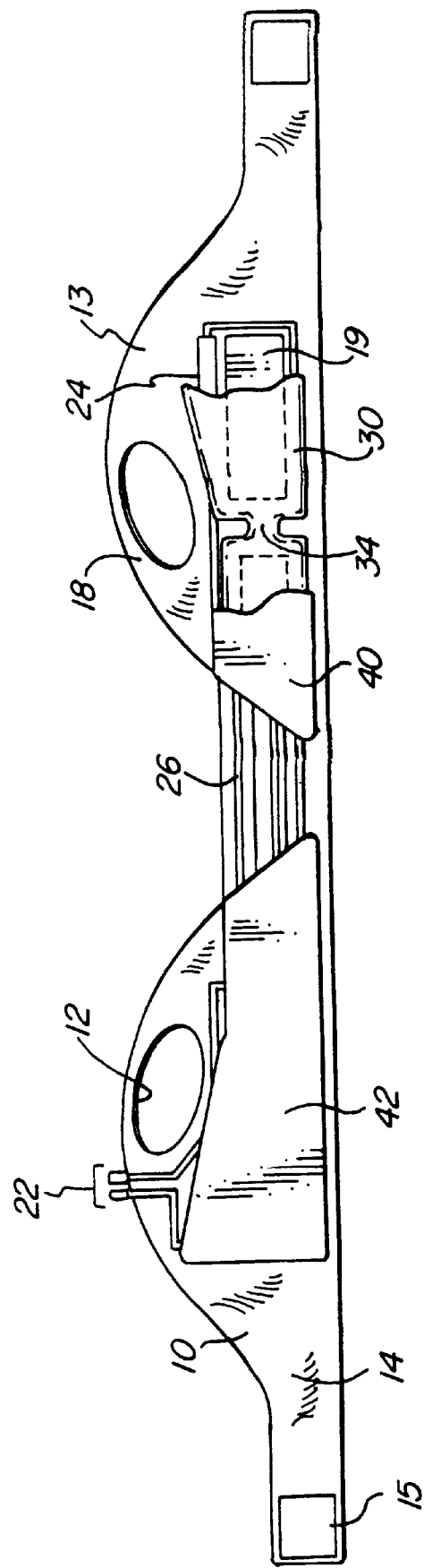
FIG. 4 is an interior cut away view of the garment device of FIG. 2 showing the layers comprising the present invention in view of the side that is applied to the patient's head.

Referring to FIGS. 2 and 3, the device of the present invention comprises the anatomically designed fabric layer 10 wherein a hard malleable plate 19 is attached to fabric layer 10 either by adhering the plate 19 to the fabric, such as for example and not as a limitation to the present invention, by stitching or with VELCRO®, or any other means known in the art, suitable for the application, or alternatively by inserting the plate in a pouch formed in fabric layer 10, thereby allowing removal of plate 19. Preferably, an additional plate 19a is also attached to fabric layer 10 as shown in FIG. 3. Plates 19 and 19a can be of any hard material so as to resist bulging of fabric layer 10 when a pressure of about 30 mm to about 35 mm of Hg/cm is applied. The plates 19 and 19a should also be malleable or flexible so that they can bend to the contour of the patient's jaw area, if needed. Plates 19 and 19a of such a construction can render the device of the present invention effective in directing the desired compression to the maxillomandibular region of the patient. Suitable materials for plates 19 and 19a are some conventional metals and plastics, most preferably a thermally conductive cold polymer, such as polyethylene reinforced with thin stainless steel strips, which could be cooled or heated externally prior to application to fabric layer 10. The fabric layer 10 is most preferably of a material that can be sterilized before and after use, is water repellant, and is not radioopaque such that x-rays may be taken of a patient's head without removing the fabric layer 10. Suitable materials for fabric layer 10 are: neoprene and polyester, woven polyester or nylon. The most preferred material is attached neoprene and polyester. The most preferred thickness for fabric layer 10 is about 0.6 mm to 1.2 mm, and for plates 19, about 1.2 mm to 2.2 mm.

Over the fabric layer 10, and plates 19, is placed a heater 26 comprising a heating element 24 and connecting wires terminating at leads 22 for connection to a power source, such as a 12 volt battery. The leads 22 exit the device of the present invention behind one of the auricular regions 12 of fabric layer 10. The placement of heater 26 over fabric layer 10 is such that it should heat the masticatory muscles, the temporomandibular joint and temporal regions of the patient. Preferably, the heater 26 further comprises a second heating element 24a, in addition to a first heating element 24. In this embodiment, the present invention allows more direct heating to each side of the temporomandibular joint, masseter and temporal muscles. The heater 26 is a resistive type heater having a preferred thickness of about 1.2 mm to 2.2 mm. The heater 26 is attached to the fabric layer 10, preferably by stitching or by any means known in the art suitable for the application. Over the layer that heater 26 occupies is placed an inflatable layer 30. Alternatively, the inflatable layer 30 may be placed within the same layer as heater 26. The inflatable layer 30 can comprise a two-way inflation-deflation valve 32 which regulates the pressure within inflatable layer 30 to the temporomandibular joint and maxillomandibular region of the patient. By way of example, and not as a limitation to the present invention, pressures from about 30 mm to about 35 mm of mercury (Hg) per centimeter (cm) sustained in the inflatable layer 30 are operable. The inflation-deflation valve 32 also functions to allow inflation layer 30 to be inflated with a cryo gas fluid from a portable pressurized cylinder. Preferably, the inflation-deflation valve 32 is positioned behind the auricular region 12 of fabric layer 10 opposite to the position of leads 22 of heater 26. The inflatable layer 30 preferably contains a plurality of sacks that are joined by bridge 34 such that the inflation fluid in each sack can move freely into another sack. Most preferably, the inflatable layer 30 is of a material compatible with cryo gases, i.e., those gases whose temperatures are at or below 36 degrees to 39 degrees Fahrenheit, at or near ambient pressure. The most preferred material for the inflatable layer 30 is polypropylene of a thickness of about 0.8 mm for each sheet used in the deflated state. The inflatable layer 30 is constructed of a configuration which is anatomically compatible with fabric layer 10, and positions the sacks in conjunction with plates 19 such that when inflated with a fluid such as a cryo gas, a temperature of about 36 degrees Fahrenheit and a pressure of about 30 mm to about 35 mm of mercury (Hg) per centimeter (cm) can be readily maintained to the temporomandibular joint and maxillomandibular region of the patient. The inflatable layer 30 is attached to the fabric layer 10, preferably by stitching or by any other means known in the art suitable for the application.

Additional conductive layers 40 and 42 can be placed over the inflatable layer 30 to aide in better distributing the temperature generated by heater 26 and/or inflatable layer 30. What is meant by "better" temperature distribution is that the temperature generated by heater 26 and/or inflation layer 30 is conducted to cover substantially all of the temporomandibular joint and maxillomandibular region of the patient so as to offer improved pain relief and therapeutic healing conditions. The conductive layer 40 and 42 can also function to contain and cover the other aforementioned layers to the fabric layer 10 by attachment with VELCRO® strips, or by inserting the conductive layers 40 and 42 in a pouch formed in fabric layer 10, or by stitching the conductive layers 40 and 42 to fabric layer 10, or by other means known in the art suitable for the application. The conductive layers 40 and 42 can also have the advantage to increase the patient's comfort serving as a buffer layer between the layers containing the heater 26 and inflatable layer 30 and the patient's skin. Preferably, the conductive layers 40 and 42 are constructed of polyethylene of about 0.8 mm thick. Alternatively, the conductive layer may be of a single sheet.

One advantage to the present invention is that a variety of injuries to the facial region that require a reduction of temperature or an increase of temperature can be effectively treated with a single device that is portable and readily controlled by the patient.

For example, in one embodiment of the present invention that contains both a heater 26 and an inflatable layer 30, all the benefits of cryo, thermal and compression therapy can be applied. Clinical observations in the field of facial pain and temporomandibular joint disorders support that injured muscles, joints, and tendons respond favorably to initial cold therapy. Such conditions are inflammation of the temporomandibular joint or masticatory muscles. However, during the repair process, heat will provide additional blood supply and help promote healing. Such conditions are ischemia and acute pain. Compression of the injured joints, muscles, and jaw provide better, faster, and less complicated and predictable recoveries.

In an alternative embodiment of the present invention that does not contain the heater 26, cryo compression therapy can be more effectively administered to the anatomical regions as described. For example, in the cases of direct trauma to the temporomanibular joint and for the reduction of post-operative swelling and hemorrhage, the cryo compression portion of the present invention can have a favorable effect. As such, the present invention provides cold and compression specifically to the angle of the lower jaw where most traumatic injuries, such as mandibular fractures occur. The angle of the jaw is also subject to a variety of cosmetic and functional surgeries which the present invention will provide stabilization, compression, and cold to reduce post-operative swelling and hemorrhage.

Another advantage is the device has been anatomically designed to particularly treat the temporomandibular joint and its disorders, the masitcatory muscles, and generally the maxillofacial region for improved cryo, thermal, and compression therapy.

Another advantage to the configuration of the present invention is that it is a simpler and more ergonomic design which allows easier and more comfortable use by the patient in applying cryo, thermal and compression therapy. The device of the present invention is an integral, portable unit wherein the patient can readily apply any combination of cryo, thermal, or compression therapy without altering the device. Moreover, the patient can readily adjust and maintain the temperature and pressure of the unit with minimal effort and no alteration of the device itself.

Yet another advantage of the present invention is that it can also be manufactured with less cost due to its simpler layered construction, which also facilitates cleaning, maintenance, repair and part replacement.

In operation, fabric layer 10 containing the layers as described, is positioned under the lower jaw of the patient and wrapped over and around the temporomandibular joint. The patient's ears are fitted through the auricular regions 12 with the bands 18 fitted behind each ear. The straps 14 are positioned on the patient's parietal region and are then joined together by VELCRO® strips 15. The leads 22 of heater 26 are connected to a power source, and heater 26 is operated to deliver a temperature at least of about 110 degrees to 120 degrees Fahrenheit, but can be adjusted to a temperature to suit the patient's particular comfort level. Adjustment of heater 26 can be by a rheostat or any other means known in the art. The inflation-deflation valve 32 of inflation layer 30 is connected to a cryo gas source, such as a portable pressurized cylinder. The patient can regulate the flow of the gas from the gas source by a pressure regulator valve, such as a needle valve, or any other means known in the art. The temperature of the cryo gas can also be regulated by selection of the type of cryo gas and its thermodynamic properties, by an external vaporizer, or by an external heat exchanger, or any other means known in the art. The optimum minimum temperature that the device should be regulated toward is about 36 degrees Fahrenheit, but cooling to about 36 degrees to about 38 degrees Fahrenheit may be beneficial. The patient or physician can adjust the amount of gas fed to inflation layer 30 so as to create a preferred pressure of about 30 mm to about 35 mm of Hg/cm to the temporomandibular or maxillomandibular region of the head. However, the present invention is not limited to a device operating at a particular temperature or pressure and can be designed to accommodate a patient's particular comfort level or treatment regimen. Alternatively, heating and compression may be supplied from the device by introduction of a hot pressurized fluid into inflation layer 30, such as hot water. Also, compression can be provided from the device by using a hand held pump, that pumps air into inflation layer 30.

It should be understood that the foregoing is illustrative and not limiting and that obvious modifications may be made by those skilled in the art without departing from the spirit of the invention. Accordingly, reference should be made primarily to the accompanying claims, rather than the foregoing specification, to determine the scope of the invention.

What is claimed is:

1. A device to treat the temporomandibular joint of a patient comprising:
   a fabric layer anatomically configured to contact the temporomandibular joint, the chin and the parietal area of a patient, having an extension around the angle of the jaw and the temporomandibular joint;
   an inflatable layer to direct compression to the temporomandibular joint; said inflatable layer attached to said fabric layer; and
   a heater attached to said fabric layer for heating the masticatory muscles, the temporomandibular joint and temporal regions; said inflatable layer being compressible to conform to the contour of the patient's facial region extending between the temple and jaw and to direct compression to the temporomandibular joint.

2. A device according to claim 1, wherein said fabric layer is of a material that can be sterilized, is water repellent, and is not radioopaque.

3. A device according to claim 2, wherein said inflatable layer has a plurality of sack regions.

4. A device according to claim 3, wherein said heater is lateral to, and positioned in the same layer as said inflatable layer.

5. A device according to claim 4, wherein said heater further comprises a first heating element and a second heating element, said first heating element being positioned on said fabric layer to contact one side of the temporomandibular joint and temporal regions, said second heating element being positioned on said fabric layer to contact another side of the temporomandibular joint and temporal regions, wherein said first and second heating elements provide direct heat to each side of the temporomandibular joint, masseter and temporal muscles.

6. A device according to claim 1 wherein the inflatable layer has an outer edge surrounded by the fabric layer.

7. A device to treat the temporomandibular joint of a patient comprising:
   a fabric layer anatomically configured to contact the temporomandibular joint, the chin and the parietal area of a patient, having an extension around the angle of the jaw and the temporomandibular joint;
   an inflatable layer to direct compression to the temporomandibular joint; said inflatable layer attached to said fabric layer;
   a heater for heating the masticatory muscles, the temporomandibular joint and temporal regions; said heater attached to said fabric layer;
   a heat conductive layer covering said inflatable layer; and
   a hard plate placed on said fabric layer, wherein said plate is lateral to the patient's skin to resist bulging of said inflatable layer when inflated.

8. A device to treat the maxillomandibular region of a patient comprising;
- a fabric layer anatomically configured to contact the maxillomandibular region, the chin and the parietal area of a patient, having an extension around the angle of the jaw;
- an inflatable layer to direct compression to the maxillomandibular region; said inflatable layer attached to said fabric layer; and
- a hard plate removably placed on said fabric layer, wherein said plate is lateral to the patient's skin to resist bulging of said inflatable layer.

9. A device according to claim 8 further comprising;
- a conductive layer covering said inflatable layer, wherein said fabric layer is of a material that can be sterilized, is water repellent, and is not radioopaque.

* * * * *